US009393085B2

(12) United States Patent
Mohr

(10) Patent No.: US 9,393,085 B2
(45) Date of Patent: Jul. 19, 2016

(54) CONNECTOR FOR COUPLING AN ORTHODONTIC APPLIANCE TO A PATIENT AND ASSOCIATED METHODS

(71) Applicant: Ormco Corporation, Orange, CA (US)

(72) Inventor: Jason A. Mohr, Fontana, CA (US)

(73) Assignee: Ormco Corporation, Orange, CA (US)

( * ) Notice: Subject to any disclaimer, the term of this patent is extended or adjusted under 35 U.S.C. 154(b) by 223 days.

(21) Appl. No.: 14/207,776

(22) Filed: Mar. 13, 2014

(65) Prior Publication Data

US 2014/0272758 A1    Sep. 18, 2014

Related U.S. Application Data

(60) Provisional application No. 61/781,523, filed on Mar. 14, 2013.

(51) Int. Cl.
*A61C 3/00*    (2006.01)
*A61C 7/36*    (2006.01)

(52) U.S. Cl.
CPC ........................................ *A61C 7/36* (2013.01)

(58) Field of Classification Search
CPC .... A61C 7/36; A61M 39/10; A61M 39/1011; A61M 39/1016; A61M 39/20
USPC ........................... 433/18, 19, 21, 24, 177, 178
See application file for complete search history.

(56) References Cited

U.S. PATENT DOCUMENTS

| | | | |
|---|---|---|---|
| 3,618,214 A | 11/1971 | Armstrong |
| 3,798,773 A | 3/1974 | Northcutt |
| 4,462,800 A | 7/1984 | Jones |
| 4,618,324 A | 10/1986 | Nord |

(Continued)

FOREIGN PATENT DOCUMENTS

| | | |
|---|---|---|
| DE | 20116895 U1 | 12/2001 |
| JP | 61047098 | 10/1986 |

(Continued)

OTHER PUBLICATIONS

Laure Acquaviva (Authorized Officer); Partial Search Report for PCT/US2007/000618; Jul. 2, 2007; 2 pages; European Patent Office.

(Continued)

*Primary Examiner* — Cris L Rodriguez
*Assistant Examiner* — Mirayda A Aponte
(74) *Attorney, Agent, or Firm* — Wood, Herron & Evans, LLP

(57) ABSTRACT

An orthodontic appliance includes a first connector member, selected from one of a connector element and an element receiver, and a second connector member, selected from the other of the connector element and the element receiver, is coupled to a patient. The connector element and element receiver cooperate to secure and release the orthodontic appliance to and from the patient. The connector receiver includes a housing and a clip, wherein the housing receives the connector element and the clip is movable along an axis between a release and blocked positions, but is biased toward the blocked position. The connector element is capable of being inserted into and removed from the housing when the clip is in the release position, and the connector element is captured within the housing when the clip is in the blocked position. A method for coupling an orthodontic appliance to a patient is also disclosed.

18 Claims, 6 Drawing Sheets

(56) References Cited

U.S. PATENT DOCUMENTS

| | | | |
|---|---|---|---|
| 4,795,342 A | 1/1989 | Jones | |
| 5,011,404 A | 4/1991 | Losi | |
| 5,120,218 A | 6/1992 | Hanson | |
| 5,183,388 A | 2/1993 | Kumar | |
| 5,352,116 A | 10/1994 | West | |
| 5,378,147 A | 1/1995 | Mihailowitsch | |
| 5,545,037 A | 8/1996 | Takeshi | |
| 5,562,445 A | 10/1996 | DeVincenzo et al. | |
| 5,620,321 A | 4/1997 | Thornburg et al. | |
| 5,632,618 A | 5/1997 | Jensen | |
| 5,678,990 A | 10/1997 | Rosenberg | |
| 5,711,667 A | 1/1998 | Vogt | |
| 5,738,514 A | 4/1998 | DeVincenzo et al. | |
| 5,829,975 A | 11/1998 | Gold | |
| 5,919,042 A | 7/1999 | Williams | |
| 5,944,518 A | 8/1999 | Sabbagh | |
| 5,964,588 A | 10/1999 | Cleary | |
| 5,976,774 A | 11/1999 | Uchihiro | |
| 5,980,247 A | 11/1999 | Cleary | |
| 6,012,920 A | 1/2000 | Woo | |
| 6,036,488 A | 3/2000 | Williams | |
| 6,053,730 A | 4/2000 | Cleary | |
| 6,113,390 A | 9/2000 | Sirney et al. | |
| 6,162,051 A | 12/2000 | Brehm et al. | |
| 6,168,430 B1 | 1/2001 | Higgins | |
| 6,234,792 B1 | 5/2001 | DeVincenzo | |
| 6,241,517 B1 | 6/2001 | Williams | |
| 6,290,495 B1 | 9/2001 | Jabri | |
| 6,322,357 B1 | 11/2001 | Vogt | |
| 6,328,562 B1 | 12/2001 | Sirney et al. | |
| 6,358,046 B1 | 3/2002 | Brehm et al. | |
| 6,361,315 B1 | 3/2002 | Hanks | |
| 6,402,510 B1 | 6/2002 | Williams | |
| 6,413,082 B2 | 7/2002 | Binder | |
| 6,520,722 B2 | 2/2003 | Hopper et al. | |
| 6,547,560 B1 | 4/2003 | Vazquez | |
| 6,558,160 B2 | 5/2003 | Schnaitter et al. | |
| 6,589,051 B2 | 7/2003 | Cleary | |
| 6,655,959 B2 | 12/2003 | Farzin-Nia et al. | |
| 6,669,474 B2 | 12/2003 | Vogt | |
| 6,702,575 B2 | 3/2004 | Hilliard | |
| 6,719,557 B1 | 4/2004 | Williams | |
| 6,769,910 B1 | 8/2004 | Pantino | |
| 6,877,982 B2 | 4/2005 | Williams | |
| 6,913,460 B2 | 7/2005 | Cleary et al. | |
| 6,964,566 B2 | 11/2005 | Sapian | |
| 6,976,839 B2 | 12/2005 | Lluch | |
| 6,988,888 B2 | 1/2006 | Cleary | |
| 7,578,672 B2 * | 8/2009 | Sheikh | A61C 7/36 433/19 |
| 8,348,664 B2 | 1/2013 | Sheikh et al. | |
| 2002/0025501 A1 | 2/2002 | Clark | |
| 2002/0025502 A1 | 2/2002 | Williams | |
| 2002/0031741 A1 | 3/2002 | Williams | |
| 2002/0164555 A1 | 11/2002 | Vogt | |
| 2002/0172909 A1 | 11/2002 | Williams | |
| 2003/0022124 A1 | 1/2003 | Schnaitter et al. | |
| 2003/0022125 A1 | 1/2003 | Cleary | |
| 2003/0091952 A1 | 5/2003 | Bowman et al. | |
| 2003/0157455 A1 | 8/2003 | Teramoto | |
| 2003/0207226 A1 | 11/2003 | Forster | |
| 2003/0232301 A1 | 12/2003 | Cleary et al. | |
| 2004/0219474 A1 | 11/2004 | Cleary | |
| 2005/0260533 A1 | 11/2005 | Lluch | |
| 2013/0101952 A1 | 4/2013 | Sheikh et al. | |

FOREIGN PATENT DOCUMENTS

| | | |
|---|---|---|
| JP | S62006456 | 2/1987 |
| JP | H08509644 A | 10/1996 |
| JP | H11019099 | 1/1999 |
| JP | 2002-512074 S | 4/2002 |
| JP | 2005506127 A | 3/2005 |
| WO | 9426198 A1 | 11/1994 |
| WO | 9953858 A1 | 10/1999 |
| WO | 03032859 A1 | 4/2003 |
| WO | 2004103200 A2 | 12/2004 |

OTHER PUBLICATIONS

Claudio Salvatore; International Search Report and Written Opinion for PCT/US2007/000618; Aug. 31, 2007; 14 pages; European Patent Office.

Claudio Salvatore; International Preliminary Report on Patentabiity for PCT/US2007/000618; May 19, 2008; 10 pages; European Patent Office.

Japanese Patent Office, Office Action for application 2009-288193, mailed Nov. 1, 2011; 6 pp. including English translation.

Japanese Patent Office, Office Action for application 2008-550376, mailed Nov. 1, 2011; 6 pp. including English translation.

U.S. Patent and Trademark Office, Office Action in U.S. Appl. No. 11/621,813 dated Jul. 9, 2008.

U.S. Patent and Trademark Office, Office Action in U.S. Appl. No. 11/621,813 dated Feb. 6, 2009.

U.S. Patent and Trademark Office, Notice of Allowance in U.S. Appl. No. 11/621,813 dated Jun. 2, 2009.

U.S. Patent and Trademark Office, Office Action in U.S. Appl. No. 12/540,423 dated Mar. 24, 2011.

U.S. Patent and Trademark Office, Office Action in U.S. Appl. No. 12/540,423 dated Jan. 6, 2012.

U.S. Patent and Trademark Office, Notice of Allowance in U.S. Appl. No. 12/540,423 dated Sep. 10, 2012.

* cited by examiner

CONNECTOR FOR COUPLING AN ORTHODONTIC APPLIANCE TO A PATIENT AND ASSOCIATED METHODS

CROSS-REFERENCE TO RELATED APPLICATIONS

The present application is related to U.S. Pat. Nos. 7,578,672 and 8,348,664, entitled "ORTHODONTIC DEVICE AND METHOD FOR TREATING MALOCCLUSIONS," the disclosures of which are expressly incorporated by reference herein in their entireties. This application is related to U.S. application Ser. No. 13/708,523 filed on Dec. 12, 2012, and claims priority to U.S. Provisional Patent Application Ser. No. 61/781,523, filed Mar. 14, 2013, the disclosures of which are hereby incorporated by reference herein in their entirety.

TECHNICAL FIELD

The present invention relates generally to orthodontic appliances, and more particularly to a connector for coupling an orthodontic appliance to a patient, and methods associated with connecting orthodontic appliances to a patient using such a connector.

BACKGROUND

Orthodontic treatment involves the movement of malpositioned teeth to orthodontically correct positions. In some patients, this may include correcting the alignment of the upper dental arch, or maxillary jaw, and the lower dental arch, or mandibular jaw. For example, certain patients have a condition referred to as a Class II malocclusion, or "overbite," where the lower dental arch is located an excessive distance in a rearward direction relative to the location of the upper dental arch when the jaws are closed. Other patients may have an opposite condition referred to as a Class III malocclusion, or "underbite," wherein the lower dental arch is located in a forward direction of its desired location relative to the position of the upper dental arch when the jaws are closed. Class II and Class III malocclusions are commonly corrected by movement of the lower dental arch relative to the upper dental arch. In order to minimize the overall length of time by which a patient must undergo orthodontic treatment, it is typically desirable to achieve this correction at the same time that archwires and brackets are used to move individual teeth to desired positions. For example, oftentimes the movement of the lower dental arch is achieved by applying forces to brackets, buccal tubes, archwires, anchors, bands, caps, or attachments connected to these orthodontic appliances.

A number of orthodontic appliances for treating malocclusions have been developed. One of the most popular of such orthodontic appliances is commonly referred to as a "Herbst" device. A conventional Herbst device is comprised of a telescoping sleeve and rod assembly. Typically, one component of the assembly is pivotally secured to a molar tooth in the upper arch, while the other component is pivotally secured to a bicuspid or anterior tooth in the lower arch (or a cantilever arm in the lower arch). Oftentimes, both the sleeve and rod components are pivotally secured to their respective dental arches using a screw that is inserted through an opening or eyelet in the respective components and coupled to a threaded member on the archwire, bracket, cap or other orthodontic appliance.

Herbst devices operate by forcing the lower arch into a desired occlusion position when the mouth is closed. In other words, the Herbst device prevents a patient from comfortably closing his or her mouth unless the arches are physically repositioned for proper occlusion. If the arches are not properly repositioned, the sleeve of the Herbst device impacts an end portion of the rod so as to create a hard, fixed "stop" that is uncomfortable for the patient. To compensate for this uncomfortable stop the patient repositions their mandibular jaw forward. Eventually, the patient experiences physiological adaptation based upon a learned response such that the jaws begin to naturally close with the proper occlusion. As treatment progresses, spacers may be positioned on the rod to properly reposition the hard, fixed stop once the jaws have begun to adapt, thereby permitting continued treatment and further adaptation of the jaws to the proper occlusion.

While Herbst devices are generally successful for moving the jaws over a significant distance and in a relatively short period of time, it is sometimes necessary to follow treatment using a Herbst device with treatment using a spring-biased bite corrector. For instance, it is not uncommon for the jaws to slightly relapse out of proper occlusion after treatment with a Herbst device. In these cases, the relapse is often corrected using a spring-biased bite corrector. To this end, the Herbst device is typically removed from the teeth and mouth of the patient and a separate spring-biased bite corrector is installed on the teeth.

Spring-biased bite correctors may be arranged to generate a push-type force to move the mandibular jaw or teeth forward and typically include a spring or flexible member that applies a biasing force on the mandibular jaw or teeth to achieve movement. The spring is biased when the jaws are closed such that it applies a force generally along the normal growth direction for a human jaw. The connection between a spring-biased bite corrector and the upper and lower arches is typically complex, utilizing multiple separate parts. For instance, the posterior end of the bite corrector is typically coupled to a buccal tube on an upper molar using a bayonet wire or pin which has a first end coupled to the posterior of the bite corrector and a free end that is first threaded through the buccal tube and then bent back on itself thereby coupling the posterior end to the upper arch. The anterior end of the bite corrector typically includes an eyelet, which is positioned on, and moves freely along, the archwire on the lower arch. Alternately, the anterior end of the bite corrector may be positioned on an auxiliary wire associated with the lower arch.

In addition to the above, spring-biased bite correctors may also be used in other orthodontic treatments. For example, if the malocclusion is relatively small, therefore not generally requiring significant muscular and skeletal adaptation, a spring-biased bite corrector may be used in the first instance to correct the malocclusion. Spring-biased bite correctors may also be used in the orthodontic treatment of adult patients where physiological adaptation to the jaw may be more limited.

In any event, there are some drawbacks to the current orthodontic appliances for the treatment of malocclusions as described above. For example, one drawback is that connectors that couple the orthodontic appliances to the teeth or arches may require assembling multiple separate pieces, which may be difficult and time consuming. This may be particularly true if the appliance is coupled to a molar in the posterior of the mouth, therefore having limited accessibility. Moreover, in order to maintain the connections and withstand the forces exerted during orthodontic treatment, the connectors that couple the appliances to the teeth or arches, as well as the tools used to make the connection, are often large and bulky. These components and associated tools may therefore cause patient discomfort through contact with oral tissues. In yet another drawback, current connectors, and especially screw-based connectors, provide very limited movement of the jaws in a lateral direction (i.e., left to right movements). This leads to increased device breakage, as patients attempt to move their jaws in the lateral direction, and is generally uncomfortable for the patient.

Accordingly, there is a need in the orthodontic art for improving the devices and methods for coupling orthodontic appliances to a patient.

SUMMARY

To address these and other deficiencies in the art, an orthodontic apparatus includes an orthodontic appliance configured to be coupled to a patient to facilitate orthodontic treatment and having a first connector member, and a second connector member configured to be coupled to the oral cavity of the patient. The first connector member includes one of a connector element and an element receiver and the second connector member includes the other of the connector element and the element receiver. The connector element and the element receiver cooperate to selectively secure and release the orthodontic appliance to and from the patient in an improved manner. The connector receiver includes a housing and a clip movably disposed within the housing, wherein the housing is configured to receive at least a portion of the connector element therein, and the clip is movable relative to the housing along a first linear translation axis between a release position and a blocked position. In an exemplary embodiment, the clip is biased toward the blocked position. The at least a portion of the connector element is capable of being inserted into and removed from the housing when the clip is in the release position, and the at least a portion of the connector element is captured within the housing when the clip is in the blocked position.

In one embodiment, the clip includes a body having a central aperture with a first aperture portion and a second aperture portion. The first aperture portion is larger than the second aperture portion and may intersect the second aperture portion to provide a key-hole configuration, for example. The at least a portion of the connector element is sized relative to the first and second aperture portions so as to be allowed to pass through the first aperture portion, but be prevented from passing through the second aperture portion. In one embodiment, the central aperture may be fixed in size and may further be completely surrounded or circumscribed by the body of the clip.

In one embodiment, the connector element defines a second linear translation axis, the first aperture portion defines a first aperture axis, and the second aperture portion defines a second aperture axis. When the clip is in the release position, the first aperture axis may be substantially co-linear with the second linear translation axis. Moreover, when the clip is in the blocked position, the second aperture axis may be substantially co-linear with the second linear translation axis. In one embodiment, movement of the clip from the blocked position toward the release position moves the clip along the first linear translation axis in a direction toward the housing. Conversely, movement of the clip from the release position toward the blocked position moves the clip along the first linear translation axis in a direction away from the housing.

To bias the clip toward the blocked position, the clip includes a resilient member and the housing includes an engagement wall that interact to achieve the biasing. As the clip moves toward the release position, the resilient member contacts the engagement wall to deform the resilient member and generate a force urging the clip back toward the blocked position. In one embodiment, the resilient member includes at least one spring arm having a first end coupled to a body of the clip and a second free end extending therefrom, and the engagement wall includes an arcuate section. As the clip is moved toward the release position, the at least one spring arm is urged toward the clip body due to its engagement with the arcuate section. In one embodiment, when the clip is in the blocked position, the resilient member contacts the engagement wall to generate a threshold force urging the clip away from the release position. Thus, a force greater than the threshold force must be applied to the clip in order to move the clip from the blocked position toward the release position.

To minimize the buccal-lingual extent of the connector, the housing may include an end wall having an opening configured to receive the at least a portion of the connector element. When the orthodontic appliance is secured to the patient, the at least a portion of the connector element projects into the opening but does not extend beyond the end wall. Thus, part of the length of the connector element is taken up by the thickness of the end wall. In another aspect, the orthodontic apparatus may include a retaining mechanism configured to limit the travel of the clip along the first linear translation axis so as to prevent the separation of the clip from the housing. Furthermore, in one particular embodiment, the orthodontic appliance may include a Herbst device.

A method of coupling an orthodontic appliance, having a first connector member selected from one of a connector element and an element receiver, to a patient includes initially coupling a second connector member to the patient. The second connector member is selected from the other of the connector element and the element receiver. The element receiver includes a housing and a clip movably disposed within the housing. The housing is configured to receive at least a portion of the connector element therein and the clip is movable relative to the housing along a first linear translation axis between a release position and a blocked position. The clip is biased toward the blocked position. From this framework, the method further includes applying a force to the clip and moving the clip from the blocked position to the release position against the bias as a result of the applied force. Once in the release position, the at least a portion of the connector element may be inserted into the housing. Subsequently, the applied force on the clip may be released so as to move the clip from the release position to the blocked position under the bias. In the blocked position, the at least a portion of the connector element is captured in the housing, thereby securing the orthodontic appliance to the patient.

In one embodiment, biasing the clip toward the blocked position may be achieved by engaging a resilient member of the clip with a wall of the housing such that movement of the clip toward the release position deforms the resilient member and generates a force urging the clip back toward the blocked position. Additionally, in one embodiment, moving the clip from the blocked position to the release position includes moving the clip along the first linear translation axis in a direction toward the housing. Conversely, moving the clip from the release position to the blocked position includes moving the clip along the first linear translation axis in a direction away from the housing. A threshold level of bias away from the release position may be maintained when the clip is in the blocked position to prevent or reduce the likelihood of unintentional decoupling of the connector members. Still further, in one embodiment the travel of the clip relative to the housing may be limited to prevent the clip from being separated from the housing.

In a further embodiment, the clip includes a central aperture having a first aperture portion defining a first axis, and a second aperture portion defining a second axis, wherein the first aperture portion is larger than the second aperture portion and intersects the second aperture portion. Additionally, the connector element defines a second linear translation axis. In accordance with the method, moving the clip from the blocked position to the release position includes aligning the first axis of the first aperture portion with the second linear translation axis. Similarly, moving the clip from the release position to the blocked position includes aligning the second axis of the second aperture portion with the second linear translation axis.

These and other objects, advantages and features of the invention will become more readily apparent to those of ordinary skill in the art upon review of the following detailed description taken in conjunction with the accompanying drawings.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the principles of the invention.

DETAILED DESCRIPTION

Figure 1:
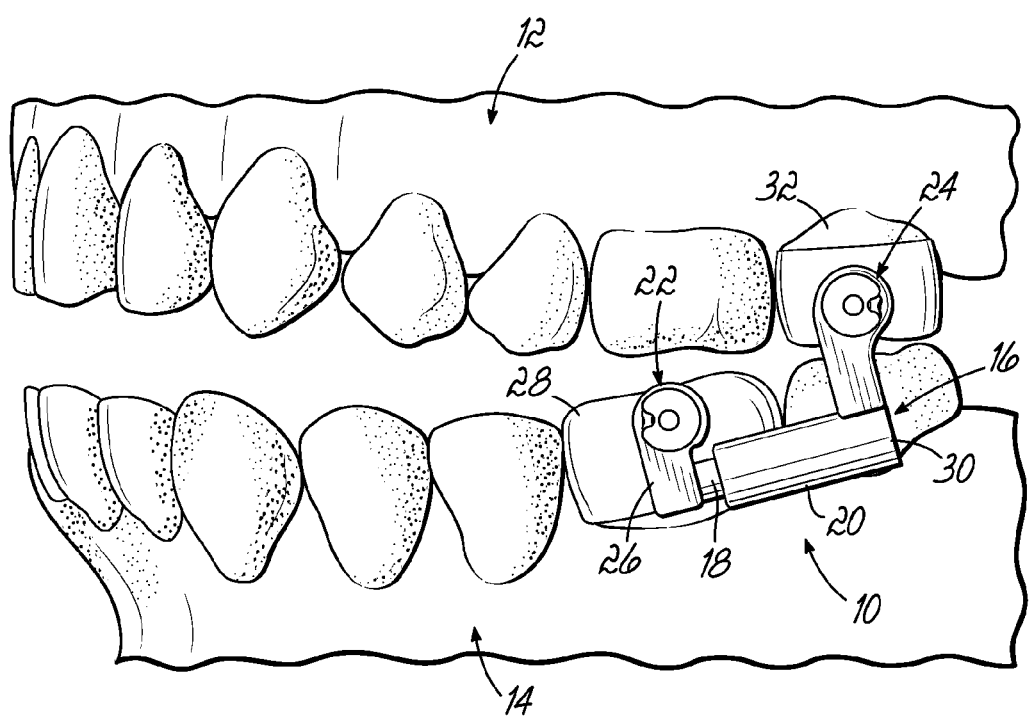
FIG. 1 is a side view of an orthodontic appliance coupled to the teeth of a patient in accordance with an embodiment of the invention.

Referring to FIG. 1, an orthodontic appliance 10 according to one embodiment of the invention may be coupled to the upper dental arch, or maxillary jaw 12, and the lower dental arch, or mandibular jaw 14, so as to reposition the mandibular jaw 14 relative to the maxillary jaw 12 and therefore correct a malocclusion, such as a Class II malocclusion. As shown, the orthodontic appliance 10 may reside generally parallel to a buccal plane that is defined by the buccal surfaces of the posterior teeth of the mandibular and/or maxillary arch. The orthodontic appliance 10 may, in one embodiment, be in the form of a Herbst device and include a telescoping rod assembly 16 comprising one or more inner rods 18 movable relative to an outer sleeve 20. The orthodontic appliance 10 may be coupled to the patient using connectors, generally shown at 22, 24, designed in accordance with aspects of the invention. For example, as illustrated, a mesial end 26 of the appliance 10 defined by the inner rod 18 may be coupled to a tooth 28, such as a molar tooth, on the mandibular jaw 14 using connector 22. Similarly, a distal end 30 of the appliance 10 defined by the outer sleeve 20 may be coupled to a tooth 32, such as a molar tooth, on the maxillary jaw 12 using connector 24. The telescoping rod assembly 16 allows the orthodontic appliance 10 to expand and contract as the jaws 12, 14 open and close.

While FIG. 1 illustrates the orthodontic appliance 10 as a Herbst device, this is merely exemplary and the orthodontic appliance 10 may include a broad range of orthodontic-based devices, including without limitation, spring-biased devises, bite jumpers, and temporary attachment devices (TADs). It should also be realized that while the appliance 10 illustrated in FIG. 1 is coupled to a tooth in each of the jaws 12, 14, aspects of the invention are not so limited. In this regard, the orthodontic appliance 10 may be coupled to other features in the oral environment including brackets, bands, buccal tubes, archwires, anchors, caps or other hardware attached to the gingiva or teeth of the patient. In its broadest aspects, the invention encompasses coupling an orthodontic appliance to a certain location in the oral environment via a connector as more fully disclosed below. Thus, while aspects of the invention will be described in the context of a Herbst device coupled to the teeth on opposing jaws of the patient, the invention should not be so limited.

In one aspect of the invention, the orthodontic appliance 10 may be coupled to the maxillary and mandibular jaws 12, 14 in an improved manner. Specifically, upper and lower connectors 22, 24 may be configured as an assembly, devoid of screws, bayonet pins, auxiliary wires or other detached parts, which may be selectively coupled to or removed from the upper and lower dental arches in a quick and convenient manner. The connectors 22, 24 may be similar in construction and function, thus only one connector will be described in detail.

Figure 2:
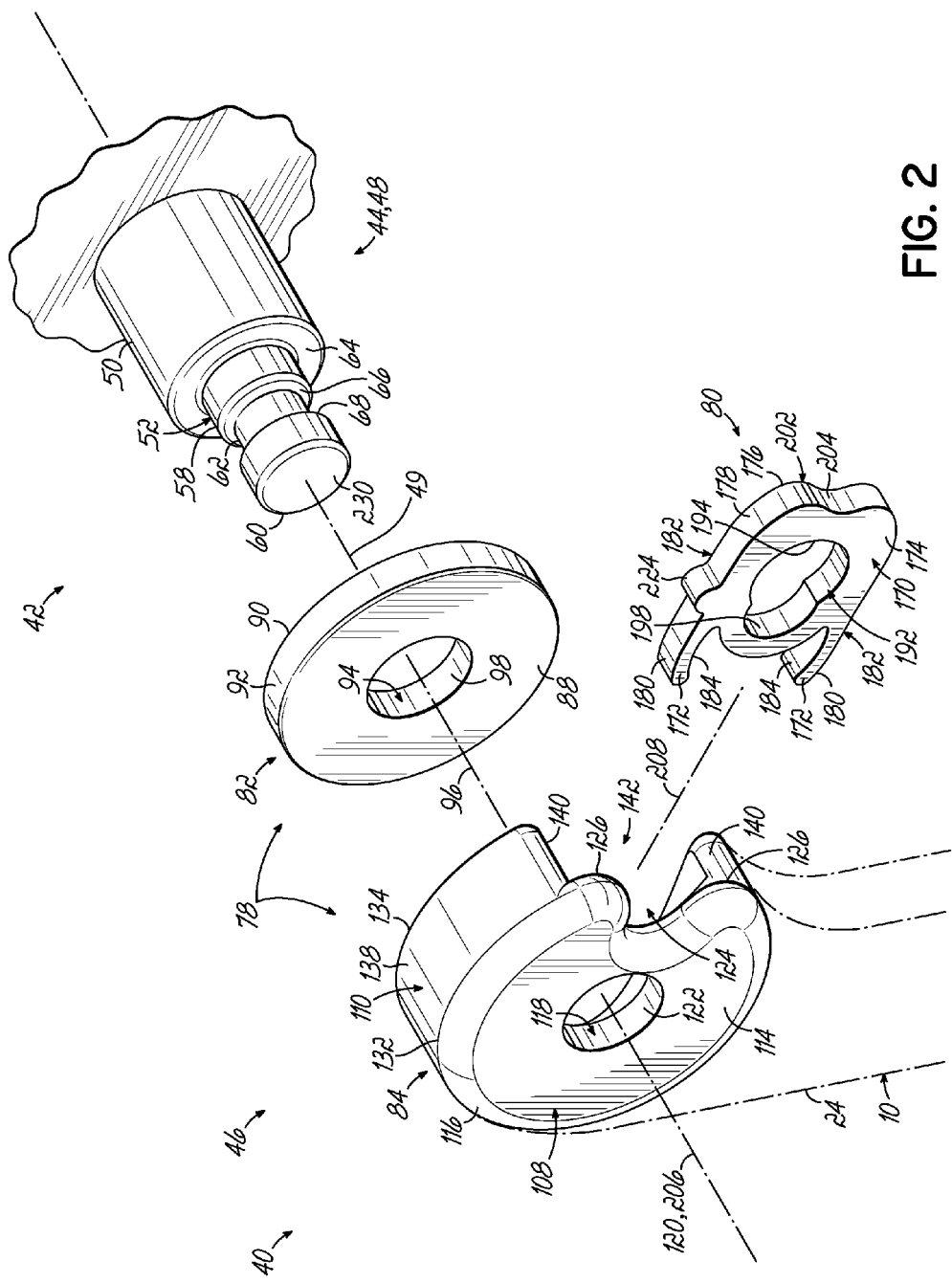
FIG. 2 is a disassembled perspective view of a connector in accordance with an embodiment of the invention for coupling the orthodontic appliance to the patient.
Figure 5:
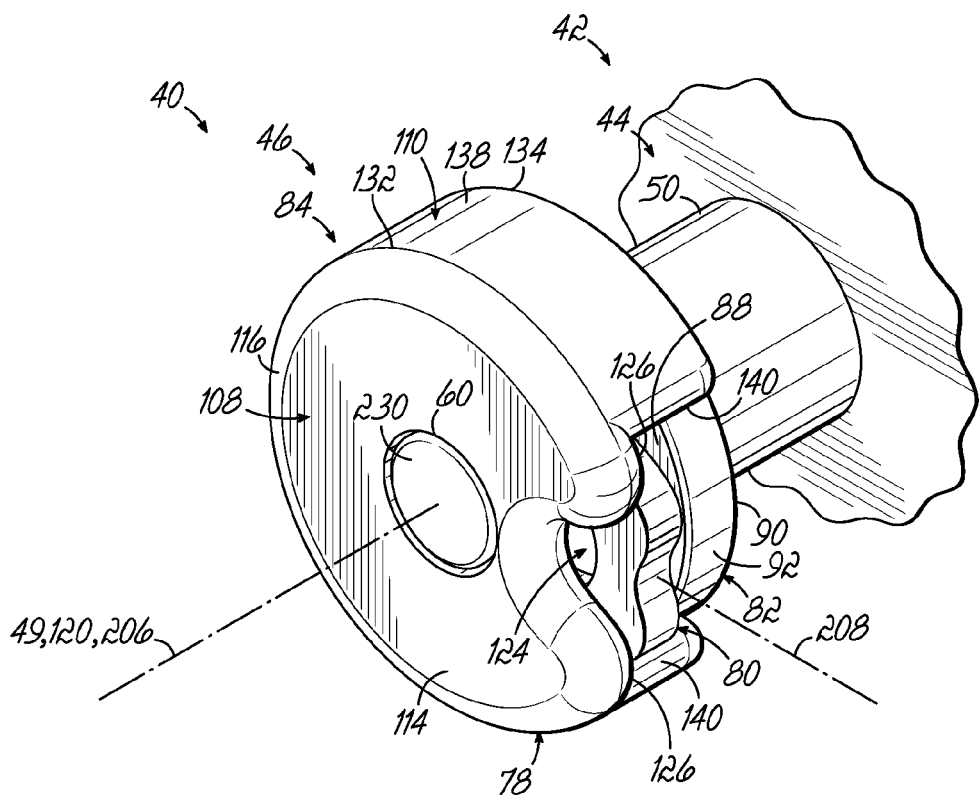
FIG. 5 is a perspective view of the embodiment shown in FIG. 2 after the orthodontic appliance is coupled to the patient.
Figure 4:
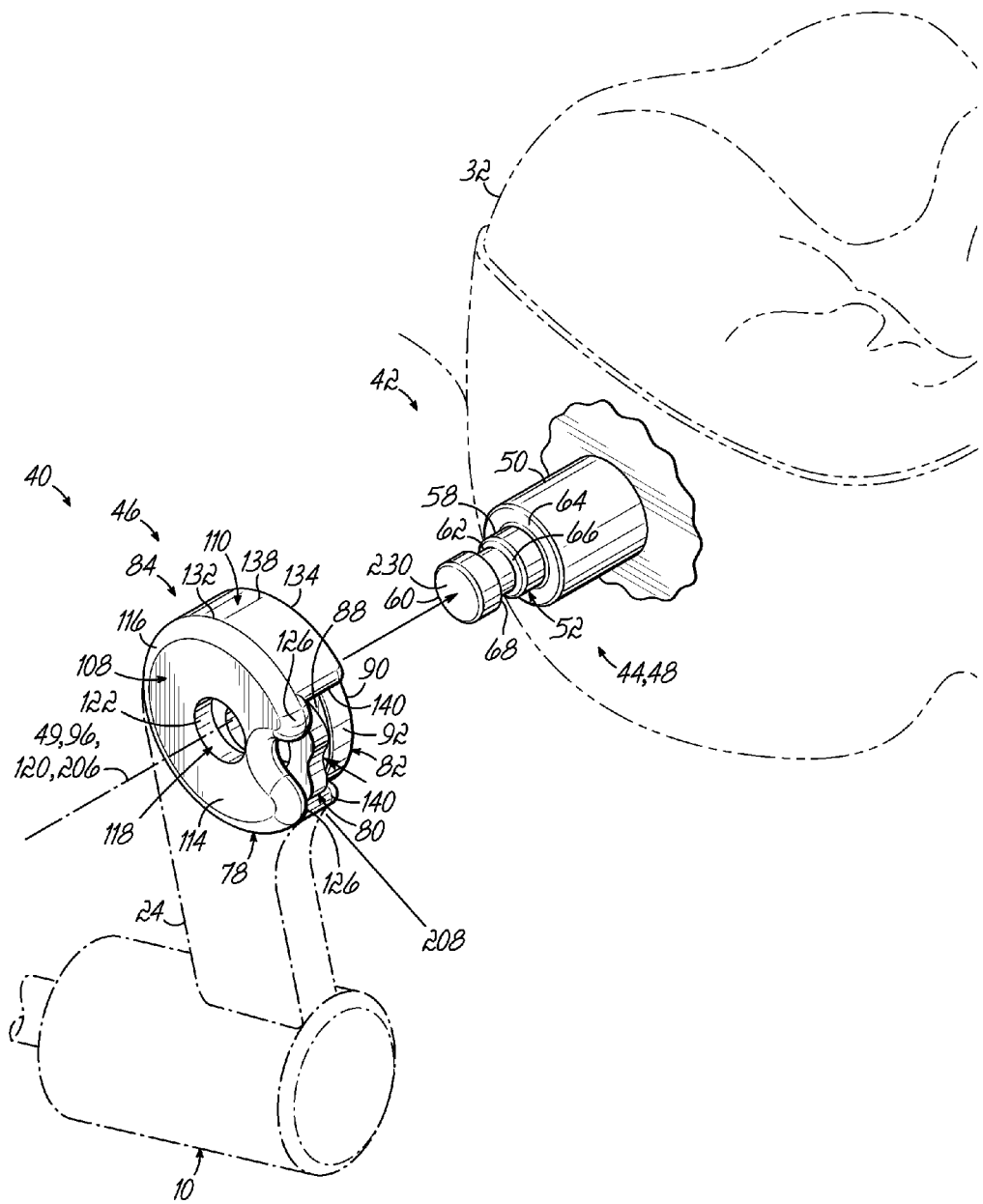
FIG. 4 is a perspective view of the embodiment shown in FIG. 2 prior to coupling the orthodontic appliance to the patient.

As shown in FIGS. 2, 4 and 5, to achieve a connection between the orthodontic appliance 10 and the patient, connector 24 includes a first connector member 40 associated with orthodontic appliance 10 and a second connector member 42 associated with the patient. For example, the second connector member 42 may be directly or indirectly coupled to a tooth, bracket, archwire, buccal tube, band, anchor, cap, or other device in the oral environment. Similarly, the first connector member 40 may be directly or indirectly coupled to the orthodontic appliance 10. The first and second connector members 40, 42 cooperate in a manner that selectively secures the orthodontic appliance 10 to the patient.

In accordance with one embodiment of the invention, the first connector member 40 may be one of a connector element 44 and an element receiver 46, and the second connector member 42 may be the other of the connector element 44 and an element receiver 46. For example, as illustrated in FIG. 2, the connector element 44 may be associated with the patient, such as on a tooth, archwire, etc., and the element receiver 46 may be associated with the orthodontic appliance 10. This arrangement is merely exemplary, as in alternative embodiments the connector element 44 may be associated with the orthodontic appliance 10 and the element receiver 46 may be associated with the patient (not shown).

As best illustrated in FIGS. 2 and 4, the connector element 44 may take the form of a post or stem 48 that projects from the patient (such as from a tooth in a facial (e.g., buccal) direction, etc.) along a connector element axis 49 and is configured to be selectively captured in and released from the element receiver 46 associated with the orthodontic appliance 10, as discussed more fully below. In one embodiment, the stem 48 includes an enlarged portion (e.g., head) adjacent to a narrowed portion (e.g., neck) that facilitates capture of the stem 48 in the element receiver 46. In this regard, the stem 48 may include a base portion 50 closest to the patient and extending therefrom, and a shaft portion 52 extending from the base portion 50. In one embodiment, the base portion 50 may be generally cylindrical and have a generally circular cross-sectional profile. However, other cross-sectional shapes and configurations may also be possible. The shaft portion 52 includes a first end coupled to the base portion 50 and a second end that projects away from the base portion 50 and patient. In one embodiment, the shaft portion 52 may have a dumbbell configuration including an inner foot 58 adjacent the first end, an outer head 60 adjacent the second end, and a neck 62 extending therebetween. The shaft portion 52 may similarly be generally cylindrical and have a generally circular cross-sectional profile. However, other cross-sectional shapes and configurations may also be possible.

Figure 6:
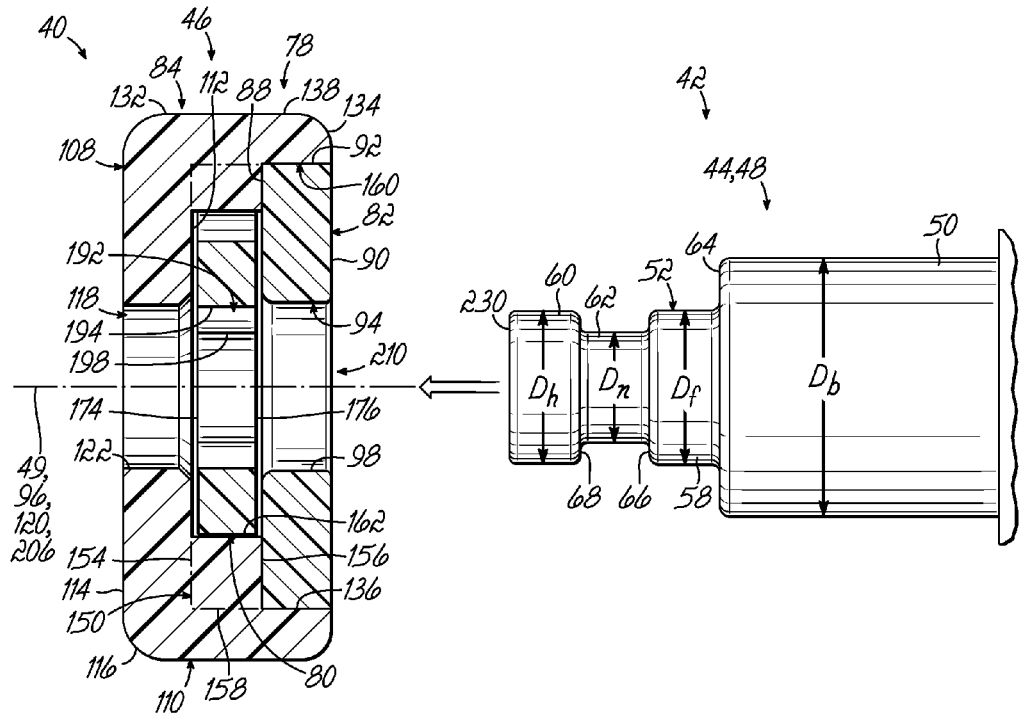
FIG. 6 is a cross-sectional view of the embodiment shown in FIG. 2 prior to coupling the orthodontic appliance to the patient.

As perhaps best shown in FIG. 6, the cross dimension of the shaft portion 52 may be generally less than the cross dimension of the base portion 50 to define a first shoulder 64. For example, a diameter $D_f$ of the inner foot 58 may be less than a diameter $D_b$ of the base portion 50 such that the first shoulder 64 may be configured as an annular ring. Additionally, the cross dimension of the neck 62 may be generally less than the cross dimension of both the inner foot 58 and outer head 60 to define respective second and third shoulders 66, 68. For example, the diameter of the neck $D_n$ may be less than the diameter $D_f$ of the inner foot 58 and the diameter $D_h$ of the outer head 60 such that the second and third shoulders 66, 68 may be configured as annular rings. Moreover, in one embodiment the inner foot 58 and outer head 60 may have the same cross dimension (e.g., diameter), although the invention is not so limited. For example, the inner foot 58 may have a cross dimension (e.g., $D_f$) greater than or less than the cross dimension of the outer head 60 (e.g., $D_h$).

While the above describes the connector element 44 as having a base portion 50 extending away from the patient, it should be recognized that in an alternative embodiment (not shown), the base portion 50 may be omitted such that the shaft portion 52 extends from the patient and the first shoulder 64 is essentially formed by a surface to which the shaft portion 52 is attached (e.g., cap, band, tooth surface, etc.). Other arrangements for the connector element 44 may also be possible to provide an enlarged portion adjacent to a narrowed portion. The connector element 44 may be formed from stainless steel or some other metal suitable for the oral environment. The connector element 44 may alternatively be formed from other materials, such as suitable plastics or the like.

Figure 8:
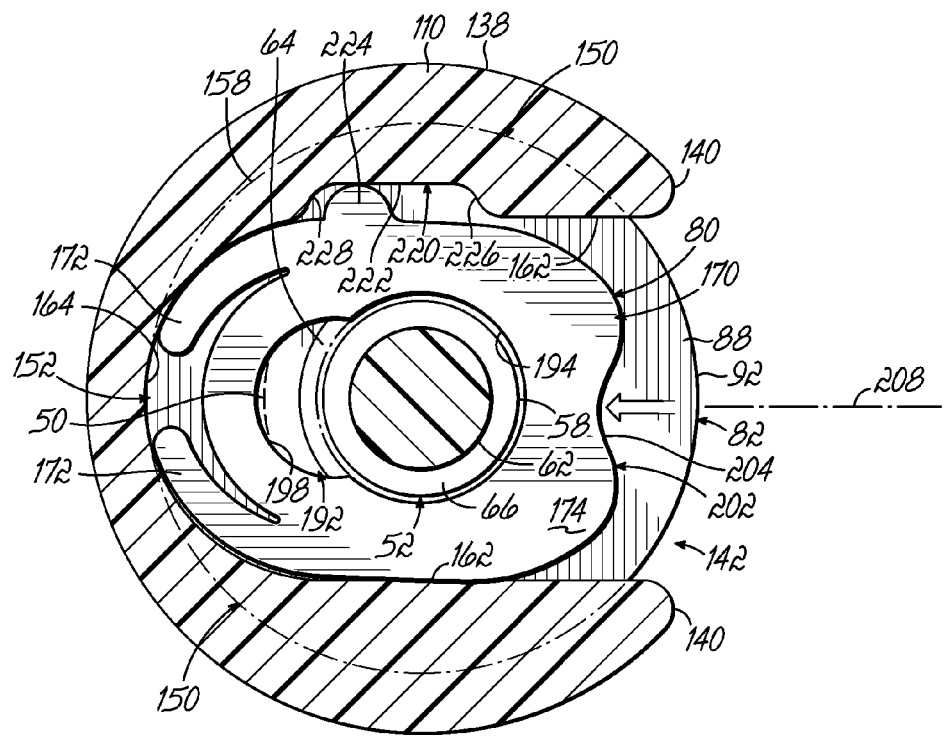
FIG. 8 is a cross-sectional view illustrating the clip in the release position.

The element receiver 46 includes a housing 78 and a clip 80 movably disposed within the housing 78 and configured to engage with the connector element 44 (FIG. 5). In accordance with aspects of the invention, the clip 80 is movable relative to the housing 78 between a blocked position (FIG. 9) and a release position (FIG. 8). In the release position, at least a portion of the connector element 44 is able to be inserted into and removed from the housing 78. In the blocked position, the connector element 44 is not able to be removed or separated from the housing 78 (once positioned therein). The connector element 44 is also prohibited from fully entering the housing 78 when in the blocked position (if the connector element is not initially positioned therein). Thus, the orthodontic appliance 10 is configured to be coupled to and removed from the patient when the clip 80 is in the release position and the orthodontic appliance 10 is configured to be securely coupled to the patient when the clip 80 is in the blocked position (and the connector element is positioned therein).

In one embodiment, the housing 78 has a two-part construction including a base member 82 and a cap member 84 coupled to the base member 82 so as to define a housing interior 86. The clip 80 may be disposed in the housing interior 86. In an exemplary embodiment, the base member 82 may be generally disk-shaped defining generally planar and parallel inner and outer faces 88, 90, and an outer side surface 92 extending therebetween. The base member 82 may be generally cylindrical and have a generally circular cross-sectional profile. Other shapes and configurations may also be possible, however, depending on, for example, how the element receiver is incorporated into the orthodontic appliance 10. The base member 82 may further include a central aperture 94 extending through the full thickness of the base member 82 so that the connector element 44 may access the housing interior 86. The central aperture 94 may be generally circular in shape and define a base member central axis 96 and an inner surface 98 extending between the inner and outer faces 88, 90. In other words, in one embodiment the base member 82 may have the appearance of an annular ring or washer. Additionally, the base member 82 may be formed from stainless steel, or other metals, plastics, etc. suitable for the oral environment.

Figure 7:
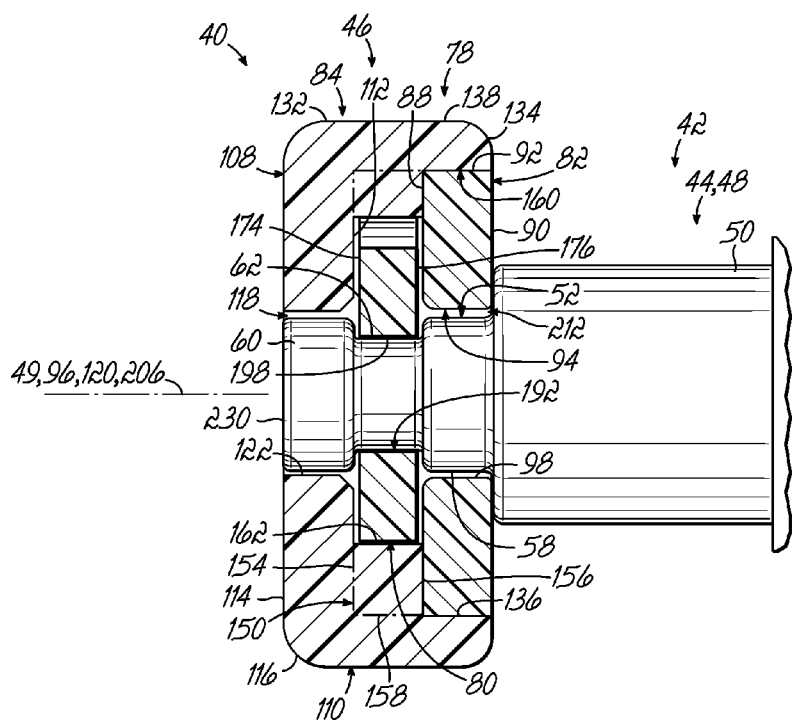
FIG. 7 is a cross-sectional view of the embodiment shown in FIG. 2 after the orthodontic appliance is coupled to the patient.

In an exemplary embodiment, the cap member 84 may include a generally cylindrical body having a generally planar end wall 108 and a side wall 110 projecting therefrom and extending along at least a portion of the periphery of the end wall 108. The end wall 108 includes an inner face 112, an outer face 114 opposite thereto, and an outer side surface 116 extending between the inner and outer faces 112, 114 (FIGS. 6 and 7). In one embodiment, the outer side surface 116 may be radiused or arcuate to avoid sharp corners and increase patient comfort. Alternatively, however, the outer side surface 116 may also be flat (not shown). The end wall 108 further includes a central aperture 118 extending through the full thickness of the end wall 108. As discussed below, the central aperture 118 is configured to receive the outer head 60 of connector element 44 to reduce the buccal-lingual profile of the connector, and thus increase patient comfort (FIGS. 5 and 7). The central aperture 118 may be generally circular in shape and define a cap member central axis 120 and an inner side surface 122 extending between the inner and outer faces 112, 114. In other words, and similar to the base member 82, in one embodiment the end wall 108 may have the appearance of an annular ring or washer (but perhaps with a radially arcuate outer edge).

In an exemplary embodiment, the end wall 108 further includes a generally U-shaped cutout 124, which may extend from the outer side surface 116 toward the central aperture 118, but does not extend so far as to intersect with the central aperture 118. The cutout 124 may be configured to smoothly meet the periphery of the end wall 108 to define a pair of generally arcuate ears 126. Additionally, the cutout 124 may be generally symmetric about an axis that is generally coextensive with a diameter of the central aperture 118. The cutout 124, however, may have other configurations.

The side wall 110 includes a first end 132, a second end 134, an inner side surface 136, and an outer side surface 138. The first end 132 is coupled to the inner face 112 of the end wall 108 generally along its periphery such that the outer side surface 138 of the side wall 110 may be generally flush or smooth with the outer side surface 116 of the end wall 108. As illustrated in the figures, the side wall 110 may extend from the end wall 108 in a generally perpendicular manner, although not so limited, and may terminate at its second end 134 with a generally radiused or arcuate configuration. In an exemplary embodiment, the side wall 110 does not extend along the full peripheral length or perimeter of the end wall 108 (FIGS. 2 and 4), but instead extends for a portion of the peripheral length of the end wall 108. In this regard, the side wall 110 may be configured to stop short of the region of the cutout 124 in the end wall 108 to define two ends or edges 140 positioned adjacent respective ears 126. The edges 140 generally define an opening 142 therebetween and may be radiused or acute so as to avoid sharp edges. With this configuration, the side wall 110 may be described as being generally C-shaped. In any event, the end wall 108 and side wall 110 may generally define an interior.

In one embodiment, the cap member 84 may be formed from stainless steel or some other metal suitable for the oral environment. Alternatively, the cap member 84 may be formed from other materials, such as plastics or the like. In one embodiment, the end wall 108 and the side wall 110 may be formed as an integral body through suitable processes known to those of ordinary skill in the art. Alternatively, the end wall 108 and the side wall 110 may be formed separately and then coupled together, such as through welding, bonding, etc., to form the cap member 84.

A retaining member 150 may be disposed in the interior of the cap member 84 and configured to receive the clip 80 therein. More particularly, the retaining member 150 may define, at least in part, a cavity 152 configured to receive and interact with clip 80 in a manner that allows the connector element 44 to be secured to and released from the element receiver 46, as will be discussed more fully below. The retaining member 150 may have an outer face 154 coupled to or adjacent the inner face 112 of the end wall 108, an inner face 156 opposite the outer face 154, and an outer side surface 158 extending therebetween and coupled to or adjacent the inner side surface 136 of the side wall 110. In one embodiment, the retaining member 150 does not extend the full height of the side wall 110, but stops short of the second end 134 thereof to define a recess 160 bounded on the sides by the side wall 110 and bounded from below, at least in part, by the inner face 156 of the retaining member 150. As described below, the recess 160 is configured to receive the base member 82 therein when the element receiver 46 is assembled (FIGS. 6 and 7).

The retaining member 150 may be integrally formed with the cap member 84 when, for example, the cap member 84 is formed as an integral body. Alternatively, the retaining member 150 may be formed integrally with either the end wall 108 or the side wall 110 when, for example, those walls are formed separately and subsequently coupled together. Still further, in one embodiment, the retaining member 150 may be formed separate from both the end wall 108 and the side wall 110 and subsequently coupled to the interior 144 of the cap member 84 through, for example, welding, bonding, etc. The retaining member 150 may be formed from stainless steel or some other metal suitable for the oral environment. Alternatively, the retaining member 150 may be formed from other materials, such as plastics or the like.

Figure 9:
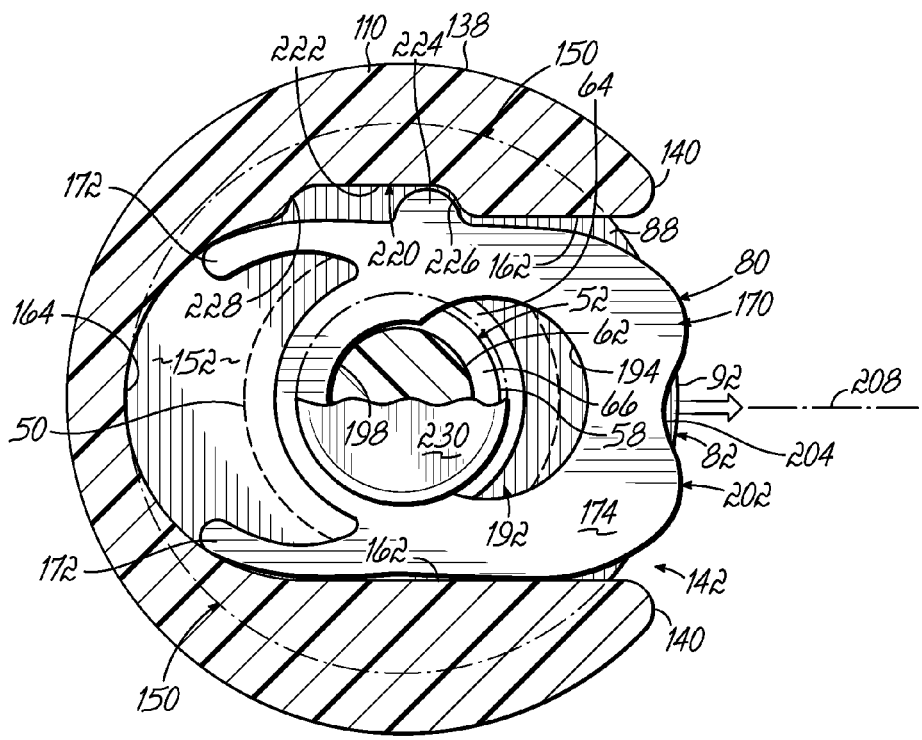
FIG. 9 is a cross-sectional view illustrating the clip in the blocked position.

As noted above, the retaining member 150 includes a cavity 152 formed therein which is configured to receive the clip 80 (FIGS. 8 and 9). The cavity 152 may be shaped in a manner that interacts with the clip 80 to achieve certain aspects of the invention. In this regard, and in an exemplary embodiment, the cavity 152 may be generally U-shaped having a pair of generally parallel straight sections 162 coupled at an end thereof by an arcuate section 164, which in one embodiment may be configured generally as a semicircle. A terminating end of the straight sections 162 intersects with the edges 140 of the side wall 110 such that the opening 142 defined thereby communicates with the cavity 152 of the retaining member 150. The opening 142 defined by the edges 140 of the side wall 100 also communicates with the recess 160. In one embodiment, the cavity 152 may be bounded by the inner face 112 of the end wall 108, and thereby open to the central aperture 118. Additionally, the cavity 152 may also be open to the recess 160.

Figure 3:
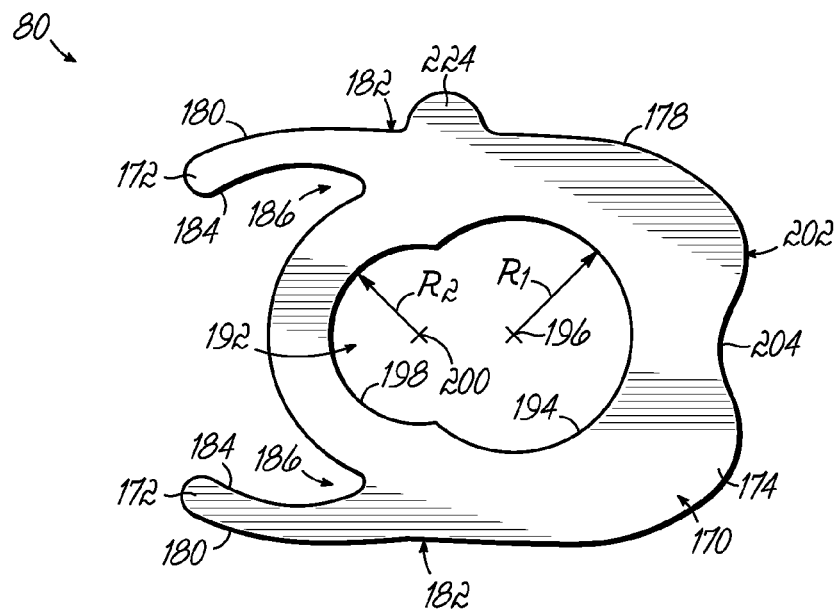
FIG. 3 is a side view of a clip in accordance with the embodiment shown in FIG. 2.

As noted above, the clip 80 is movably disposed in the housing 78, and more particularly in cavity 152, and includes a generally oblong main body 170 and at least one, and preferably two, spring arms 172 extending away from the main body 170, as best illustrated in FIG. 3. In an exemplary embodiment, the spring arms 172 extend away from the main body 170 so as to generally lie within the plane defined by the main body 170. The main body 170 includes generally planar, parallel first and second faces 174, 176 and an outer side surface 178 extending therebetween. The spring arms 172 extend from a first end of the main body 170 such that an outer side surface 180 of the spring arms 172 and the outer side surface 178 of the main body 170 generally form straight sections 182. However, an inner side surface 184 of the spring arms 172 forms a space or gap 186 with the main body 170 to provide sufficient space to allow the spring arms 172 to flex during use, as discussed more fully below.

As illustrated in the figures, in an exemplary embodiment the spring arms 172 are not straight, but may be slightly curved inwardly (such as adjacent to free ends thereof) toward the main body 170. This may provide, for example, a preferred direction of flexing for the spring arms 172. The clip 80 may be formed from a suitable material, such as spring steel, or other materials providing some level of flexing to the spring arms 172 while also providing some strength and rigidity to the main body 170. For example, the clip 80 may be formed from suitable superelastic materials, such as, nickel (Ni) titanium (Ti) alloys (NiTi), Copper (Cu) nickel (Ni) titanium (Ti) alloys (CuNiTi), and copper (Cu) aluminum (Al) nickel (Ni) alloys (CuAlNi). For example, the spring constant of the spring arms 172 may be selected to give desired properties by varying the thickness of the spring arms 172. In this way, for example, the clip 80 may be formed of a single material that provides the desired flexing of the spring arms 172 and strength and rigidity of the main body 170. Other arrangements, however, are also possible, such as forming the main body 170 of one material selected for its strength and rigidity properties, and forming the spring arms 172 of another material selected for its ability to flex. Thus, the clip 80 should not be limited to a unitary member.

The clip 80 includes a central aperture 192 extending through the full thickness of the clip 80. The central aperture 192 has a shape specifically configured to cooperate with the connector element 44 to secure and release the connector element 44 to or from the element receiver 46. In this regard, the central aperture 192 includes a first aperture portion 194 having a first central axis 196 and a first characteristic cross dimension, and a second aperture portion 198 having a central axis 200 and a second characteristic cross dimension. In an exemplary embodiment, the first and second aperture portions 194, 198 intersect with each other. Additionally, the first characteristic cross dimension is generally larger than the second characteristic cross dimension. For example, the first aperture portion 194 may be circular in shape and have a first characteristic radius of curvature $R_1$, and the second aperture portion 198 may likewise be circular in shape and have a second characteristic radius of curvature $R_2$, wherein $R_2 < R_1$. In other words, with the intersection of the first and second aperture portions 194, 198, the central aperture 192 may have a key-hole configuration. In an exemplary embodiment, the central aperture 192 may be located in the interior of the main body 170 such that the central aperture 192 is completely surrounded or circumscribed by the main body 170. Furthermore, once formed in the main body 170, the central aperture 192 may have a fixed size which does not change depending on whether the clip is in the blocked or release position.

The base member 82, cap member 84 and clip 80 may be assembled together to form the element receiver 46. In this regard, the clip 80 may be disposed in the cavity 152 of the retaining member 150. More particularly, the straight sections 182 of the clip 80 may be generally aligned with the straight sections 162 of the cavity 152 with the spring arms 172 being directed toward the arcuate section 164 of the cavity 152. With the clip 80 so disposed, the spring arms 172 may be adjacent to or alternatively engage with the arcuate section 164 of the cavity 152 (FIG. 9). Additionally, an activating end 202 of the clip 80, e.g., the end opposite to the end from which the spring arms 172 project, extends into a region adjacent to or underneath the cutout 124 in the cap member 84 (FIG. 5). In this way, the clip 80 may be accessible, such as with a tool or the like, from an exterior of the element receiver 46. In this regard, the activating end 202 may include an indentation 204 to facilitate contact with such a tool, as explained below. Furthermore, at least a portion of the central aperture 192 in the clip 80 generally overlies and is open to the central aperture 118 in the end wall 108 of the cap member 84.

The base member 82 may then be inserted into the recess 160 of the cap member 84 and coupled thereto such that the inner face 88 of the base member 82 abuts or is adjacent the inner face 156 of the retaining member 150. This coupling may be achieved through welding, bonding, or other suitable methods. The insertion of the base member 82 into the recess 160 within the cap member 84 provides for a relatively smooth or flush relationship between the outer face 90 of the base member 82 and the second end 134 of the side wall 110 of the cap member 84 (FIGS. 6 and 7). Thus, when assembled, the first face 174 of the clip 80 confronts and is bounded by the inner face 112 of the end wall 108, and the second face 176 of the clip 80 confronts and is bounded by the inner face 88 of the base member 82. Furthermore, when assembled, the central aperture 94 in the base member 82 overlies and is open to at least a portion of the central aperture 192 in the clip 80. Additionally, the central aperture 94 in the base member 82 generally aligns with the central aperture 118 in the cap member 84 such that their respective central axes 96, 120 lie along (e.g., are co-linear with) a common axis, referred to as appliance engagement/release axis 206. The relationship between the various central apertures 94, 118, 192 will be made clear below.

As discussed above, the clip 80 is movable with respect to the housing 78 between a blocked position and a release position. In one embodiment, the entire clip is moved during movement between the blocked and release positions. Due to the configuration of the clip 80 and the cavity 152 of the retaining member 150, movement of the clip 80 relative to the housing 78 may be generally restricted to translational movements along a clip translation axis 208, which may be generally perpendicular to appliance engagement/release axis 206. In the release position, the connector element 44 is able to be inserted into and removed from the housing 78. In the blocked position, the connector element 44 is not able to be removed or separated from the housing 78 (nor is the connector element 44 able to be inserted into the housing 78 when in the blocked position). For sake of discussion, the release position will be described first.

In the release position, the clip 80 is positioned relative to the housing 78 such that the first aperture portion 194 of the central aperture 192 of clip 80 generally aligns with the central apertures 94, 118 in the base member 82 and cap member 84, respectively. More particularly, in the release position, the first central axis 196 of the first aperture portion 194 lies along (e.g., is co-linear with) the appliance engagement/release axis 206. A passageway 210 defined by central apertures 94, 118 and first aperture portion 194 is sized to receive the connector element 44 therein. More specifically, the passageway 210 at least allows the outer head 60 of the connector element 44 to pass through the central aperture 192 of the clip 80 such that neck 62 of the connector element 44 generally resides within the central aperture 192 of the clip 80. In one embodiment, for example, the central aperture 118 of the cap member 84 may be sized to receive the outer head 60 of the connector element 44 therein, and the central aperture 94 of the base member 82 may be sized to receive the inner foot 58 of the connector element 44 therein. The release position is best illustrated in FIGS. 6 and 8. While there may be other arrangements as to the sizing of the various apertures and corresponding connector element portions, a key aspect is that in the release position, the outer head 60 of the connector element 44 is able to pass through the central aperture 192 of the clip 80.

Turning now to the blocked position, in the blocked position, the clip 80 is positioned relative to the housing 78 such that the second aperture portion 198 of the central aperture 192 of the clip 80 generally aligns with the central apertures 94, 118 in the base member 82 and cap member 84, respectively. More particularly, in the blocked position, the second central axis 200 of the second aperture portion 198 lies along (e.g., is co-linear with) the appliance engagement/release axis 206. A passageway 212 defined by central apertures 94, 118 and second aperture portion 198 is sized to prevent the passage of the connector element 44 therethrough. More specifically, the outer head 60 of the connector element 44 is prevented from passing through the central aperture 192 of the clip 80. In this regard, the cross dimension of the outer head 60 (e.g., $D_h$) is generally larger than the second characteristic cross dimension defined by the second aperture portion 198. The blocked position is best illustrated in FIGS. 7 and 9. Again while there may be different arrangements, a key aspect is that in the blocked position, the outer head 60 of the connector element 44 is not able to pass through the central aperture 192 of the clip 80.

In one aspect according to the invention, the clip 80 may be biased toward the blocked position such that without an intentionally imposed force acting on the clip 80, the clip 80 will normally reside in its blocked position (FIG. 9). This may be achieved, for example, through an interaction between the spring arms 172 and the cavity 152 of the retaining member 150. More particularly, in the release position, the spring arms 172 are configured to be compressed against the arcuate section 164 of the cavity 152 and flexed inwardly toward the main body 170, as shown in FIG. 8. This compression of the spring arms 172 generates a restoring force on the clip 80, generally along the clip translation axis 208 and in the direction toward the blocked position. Accordingly, without a sufficiently large externally applied force, the clip 80 tends to move from the release position toward the blocked position under the influence of the spring bias.

In contrast, in the blocked position, the spring arms 172 may have substantially no stored energy therein, i.e., substantially no compression of spring arms 172. Thus, without an externally applied force, the clip 80 will generally not move. Alternatively, however, the spring arms 172 may remain slightly compressed while in the blocked position. Maintaining some level of stored energy in the spring arms 172 when in the blocked position may be desirable such that a threshold level of force is required to initiate movement of the clip 80 from the blocked position toward the release position. This may reduce the chances of an accidental or unintentional release of the orthodontic appliance from the patient. However, in this case, a separate mechanism may be needed to maintain the position of the clip 80 in a slightly compressed state. Such a mechanism may be provided by the presence of the connector element 44 in the housing 78 (i.e., the connector element 44 helps maintain a slight compression of the spring arms 172). Alternatively, a retaining mechanism, discussed more fully below, may be provided to maintain a slight compression in the spring arms 172.

While the clip 80 is movable with respect to the housing 78, it may be undesirable to have the clip 80 separate from the housing 78. To this end, in one embodiment, the element receiver 46 may include a retaining mechanism, generally shown at 220, for retaining the clip 80 with the housing 78. The retaining mechanism is best illustrated in FIGS. 8 and 9. In one embodiment, the retaining mechanism 220 may includes a retaining slot 222 on one of the housing 78 or the clip 80, and a retaining tab 224 on the other of the housing 78 or the clip 80. The retaining tab 224 is configured to cooperate with the retaining slot 222 to prevent the separation of the clip 80 from the housing 78. More particularly, and in one embodiment, the clip 80 may include a retaining tab 224 projecting away from the main body 170, such as along one of the straight sections 182. The retaining tab 224 may also generally lie within the plane of the main body 170 in one embodiment. The retaining tab 224 may take a wide range of projecting forms, but in one embodiment, may be a formed as a generally semi-circular bump. Moreover, in one embodiment the retaining slot 222 may be formed in the inner wall that defines cavity 152 along a corresponding straight section 162. When the clip 80 is inserted into the housing 78 during assembly, the retaining tab 224 may be positioned in the retaining slot 222.

As noted above, the clip 80 is configured to move along the clip translation axis 208 between the blocked and release positions. The retaining mechanism 220 may be configured such that the retaining tab 224 is adjacent to or engages with a first end 226 of the retaining slot 222 when the clip 80 is in the blocked position. Additionally, the retaining mechanism 220 may be configured such that the retaining tab 224 is adjacent to or engages with a second end 228 of the retaining slot 222 when the clip 80 is in the release position. If a force is applied to the clip 80 along clip translation axis 208 in a direction away from the housing 78, eventually the retaining tab 224 will engage with the first end 226 of the retaining slot 222 to prohibit any further movement of the clip 80 relative to the housing 78. Accordingly, the clip 80 is prevented from separating from the housing 78.

If a force is applied to the clip 80 along clip translation axis 208 in a direction toward the housing 78, eventually the retaining tab 224 will engage with the second end 228 of the retaining slot 222 to prohibit any further movement of the clip 80 relative to the housing 78. Thus, the retaining mechanism 220 may be configured to limit the travel of the clip 80 relative to the housing 78. Additionally, as described above, the retaining mechanism 220 may be configured to maintain a slight compression of the spring arms 172 when the clip 80 is in the blocked position. In this regard, the retaining tab 224 may engage the first end 226 of the retaining slot 222 to prevent any further movement of the clip 80 while still having the spring arms 172 slightly compressed against the arcuate section 164 of the cavity 152. In other words, although the clip 80 is still under a spring bias, the retaining mechanism 220 may prevent any further movement of the clip 80 relative to the housing 78 under that spring bias.

The installation and removal of an orthodontic appliance 10 from a patient will now be described. In this regard, the connector element 44 may be coupled to the patient. For example, the connector element 44 may be coupled to a buccal surface of a patient's tooth, such as with an adhesive, cap or band (shown in FIG. 4) Alternatively, the connector element 44 may be coupled to another piece of hardware in the patient's mouth, such as, for example, an archwire, buccal tube, bracket, anchor, etc. As shown in FIG. 4, the connector element 44 may project from the tooth surface in a buccal direction such that the connector element axis 49 extends generally perpendicularly from the buccal surface of the tooth 32. In this regard, the appliance engagement release axis 206 may also extend generally perpendicularly to the buccal surface of the tooth 32. Similarly, the element receiver 46 may be coupled to the orthodontic appliance 10. This coupling may be part of the manufacturing process of the orthodontic appliance 10. For example, the cap member 84 may be integrally formed with the orthodontic appliance 10 and the clip 80 and base member 82 coupled thereto as described above. Alternatively, however, the element receiver 46 may be subsequently coupled to the orthodontic appliance 10. The orientation of the element receiver 46 is such that the base member 82 generally confronts the tooth or other support surface in the oral environment, and the cap member 84, and more particularly the end wall 108 thereof, generally faces away from the tooth or other support surface. In this way, the activating end 202 of the clip 80 may be accessible by an orthodontist or other dental professional by virtue of the cutout 124 and the opening 142 in the side wall 110. This arrangement is illustrated, for example, in FIG. 4.

Next, the clip 80 may be moved from the blocked position, which as explained above is the normal position of the clip 80, to the release position. In this regard, an orthodontist or other dental professional may engage the tip end of an orthodontic tool (not shown) with the indentation 204 in the activating end 202 of the clip 80 and apply an inwardly directed force along the clip translation axis 208 in the direction of the housing 78. The indentation 204 is configured to help stabilize the tool on the clip 80. A sufficient force is applied so as to move the clip 80 to the release position and thereby flex the spring arms 172 inwardly toward the main body 170 of the clip 80. With the clip 80 in the release position, the orthodontic appliance 10 may be moved along the appliance engagement/release axis 206 in the direction toward the patient and connector element 44. As the orthodontic appliance 10 approaches the connector element 44, the outer head 60 of the connector element 44 first passes through the central aperture 94 in the base member 82, then passes through the central aperture 192 of the clip 80 (e.g., the first aperture portion 194), and finally into the central aperture 118 of the cap member 84.

The orthodontic appliance 10 may be moved toward the patient until the outer face 90 of the base member 82 engages the first shoulder 64 of the connector element 44 (or alternatively a support surface for the connector element 44). In one embodiment, when this engagement occurs, the outer head 60 may be generally positioned in the central aperture 118 of the cap member 84, the neck 62 may be generally positioned in the central aperture 192 of the clip 80, and the inner foot 58 may be generally positioned in the central aperture 94 of the base member 82 (FIG. 7). In this regard, the thickness of the outer foot 60 and the thickness of the end wall 108 of the cap member 84 may be substantially the same, the thickness of the neck 62 and the thickness of the clip 80 may be substantially the same, and the thickness of the inner foot 58 and the base member 82 may be substantially the same. Thus, for example, the outer face 230 of the outer head 60 may be generally flush with or slightly inward of the outer face 114 of the cap member 84 when the element receiver 46 is fully positioned or seated on the element connector 44.

Once the element receiver 46 is properly seated on the element connector 44, and thus the orthodontic appliance 10 properly positioned relative to the patient, the orthodontist may release the force being applied to the clip 80 with the orthodontic tool. Of course, as the applied force is released, the spring force generated by the compression of the spring arms 172 moves the clip 80 along the clip translation axis 208 from the release position toward the blocked position. As the clip 80 moves toward the blocked position, the neck 62 of the connector element 44 enters the smaller second aperture portion 198 of the central aperture 192 of the clip 80 such that at least a portion of the first face 174 of the clip 80 underlies and confronts the third shoulder 68 of the connector element 44, and at least a portion of the second face 176 underlies and confronts the second shoulder 66 of the connector element. Accordingly, should a force be applied to the orthodontic appliance 10 along the engagement/release axis 208 and away from the patient, the third shoulder 68 will engage the at least a portion of the first face 174 of the clip 80 and substantially prevent motion along this axis and direction, thereby preventing the orthodontic appliance 10 from being removed from the connector element 44. Moreover, should a force be applied to the orthodontic appliance 10 along the engagement/release axis 208 and toward the patient, the outer face 90 of the base member 82 may engage the first shoulder 64 of the connector element 44 and substantially prevent motion along this axis and direction. Additionally or alternatively, at least a portion of the second face 176 of the clip 80 may be configured to engage the second shoulder 66 to substantially prevent motion along this axis and direction.

It should be realized that although the connector element 44 and element receiver 46 cooperate to substantially prevent movement of the orthodontic appliance 10 relative to the patient along engagement/release axis 206, the cylindrical and cross-sectional geometry of the various aspects of the connector members allows relative rotation therebetween and about this axis. Thus, the orthodontic appliance 10 may be securely fastened to the patient but is capable of pivotal movement relative to its connection.

To remove the orthodontic appliance 10 from the patient, the steps described above may be generally reversed. In this regard, an orthodontist may engage the tip end of an orthodontic tool (not shown) with the indentation 204 in the activating end 202 of the clip 80 and apply an inwardly directed force along the clip translation axis 208 in the direction of the housing 78. A sufficient force is applied so as to move the clip 80 to the release position and thereby flex the spring arms 172 inwardly toward the main body 170 of the clip 80. With the clip 80 in the release position, the orthodontic appliance 10 may be moved along the appliance engagement/release axis 206 in the direction away from the patient and connector element 44. In the release position, the outer head 60 passes through the central aperture 192 in the clip 80 and the central aperture 94 of the base member 82 such that the orthodontic appliance 10 may be removed from the patient.

Advantageously, the orientation of the clip 80 relative to the connector element 44, as described above, facilitates installation and removal of the orthodontic appliance 10. In particular and with reference to FIG. 4, the clip translation axis 208 may be generally parallel to the buccal surface of the tooth 32. This generally parallel orientation eases access to and operation of the clip 80. In this regard, the clinician may more easily reach and compress the clip 80 with a simple, controllable pinching-type motion to move the clip 80 to the release position. The orthodontic appliance 10 may then be installed and/or removed from posterior teeth while the clip 80 is compressed. This is contrasted with prior art appliances that may require unconstrained buccal-lingual pulling or tension to remove and install an orthodontic appliance. Furthermore, it will be appreciated that there is limited space between the posterior teeth and the patient's cheek that limits the installation and removal of orthodontic appliances in this area of the oral cavity. In this regard, removal and installation of the appliance 10 may be achieved by movement of the clip 80 relative to the cap member 84 in a plane parallel to the buccal surface of the tooth 32 and then a slight buccal-lingual movement of the appliance 10 so that the cap member 84 clears or engages the connector element 44 along the connector element axis 49.

While the invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. For example, while the element receiver was described herein as being incorporated into the orthodontic appliance, in an alternative embodiment, the element receiver may be a separate element (e.g., like a button or the like) which snaps on to the end of the connector element so as to sandwich or otherwise bound a portion of the orthodontic appliance about the connector element. This type of connection may increase the buccal-lingual width, but may be permissible in some applications. The invention in its broader aspects is therefore not limited to the specific details, representative apparatus and methods and illustrative examples shown and described. Accordingly, departures may be made from such details without departing from the scope or spirit of Applicant's general inventive concept.

What is claimed is:

1. An orthodontic apparatus, comprising:
an orthodontic appliance configured to be coupled to a patient to facilitate orthodontic treatment, the orthodontic appliance including a first connector member; and
a second connector member configured to be coupled to the oral cavity of the patient, wherein the first connector member includes one of a connector element and an element receiver and the second connector member includes the other of the connector element and the element receiver, the connector element and the element receiver cooperating to selectively secure and release the orthodontic appliance to and from the patient,
wherein the element receiver includes a housing and a clip movably disposed within the housing, the housing configured to receive at least a portion of the connector element therein and the clip movable relative to the housing along a first linear translation axis between a release position and a blocked position and being biased toward the blocked position, the at least a portion of the connector element capable of being inserted into and removed from the housing when the clip is in the release position and the at least a portion of the connector element captured within the housing when the clip is in the blocked position, and
wherein the clip includes a resilient member and the housing includes an engagement wall, wherein when the clip is moved toward the release position, the resilient member contacts the engagement wall to deform the resilient member and generate a force urging the clip back toward the blocked position.

2. The orthodontic apparatus of claim 1, wherein the clip includes a body having a central aperture with a first aperture portion and a second aperture portion, the first aperture portion being larger than the second aperture portion and intersecting the second aperture portion, the at least a portion of the connector element sized relative to the first and second aperture portions so as to be allowed to pass through the first aperture portion but prevented from passing through the second aperture portion.

3. The orthodontic apparatus of claim 2, wherein the central aperture is fixed in size.

4. The orthodontic apparatus of claim 2, wherein the body of the clip completely circumscribes the central aperture.

5. The orthodontic apparatus of claim 2, wherein the housing includes an aperture configured to receive the connector element therethrough, the first aperture portion being generally aligned with the aperture in the housing when the clip is in the release position and the second aperture portion being generally aligned with the aperture in the housing when the clip is in the blocked position.

6. The orthodontic apparatus of claim 1, wherein movement of the clip from the blocked position toward the release position moves the clip along the first linear translation axis in a direction toward the housing, and movement of the clip from the release position toward the blocked position moves the clip along the first linear translation axis in a direction away from the housing.

7. The orthodontic apparatus of claim 1, wherein the connector element is inserted into the housing in an insertion direction and movement of the clip from the blocked position toward the release position moves the clip in a direction that is generally perpendicular to the insertion direction.

8. The orthodontic apparatus of claim 1, wherein the resilient member includes at least one spring arm having a first end coupled to a body of the clip and a second free end extending therefrom, and wherein the engagement wall has an arcuate section, the second free end of the at least one spring arm being urged toward the clip body due to its engagement with the arcuate section.

9. The orthodontic apparatus of claim 8, wherein when the clip is in the blocked position, the resilient member contacts the engagement wall to generate a threshold force urging the clip away from the release position, wherein a force greater than the threshold force must be applied to the clip in order to move the clip from the blocked position toward the release position.

10. The orthodontic apparatus of claim 1, wherein the housing includes an end wall having an opening configured to receive the at least a portion of the connector element, wherein when the orthodontic appliance is secured to the patient, the at least a portion of the connector element projects into the opening but does not extend beyond the end wall.

11. The orthodontic apparatus of claim 1, further comprising a retaining mechanism configured to limit the travel of the clip along the first linear translation axis and thereby prevent the separation of the clip from the housing.

12. The orthodontic apparatus of claim 1, wherein the first connector member includes the element receiver and the second connector member includes the connector element.

13. The orthodontic apparatus of claim 1, wherein the orthodontic appliance includes a Herbst device.

14. A method of coupling an orthodontic appliance to a patient, the orthodontic appliance having a first connector member selected from one of a connector element and an element receiver, the method comprising:
coupling a second connector member to the patient, the second connector member selected from the other of the connector element and the element receiver, the element receiver including a housing and a clip movably disposed within the housing, the housing configured to receive at least a portion of the connector element therein and the clip movable relative to the housing along a first linear translation axis between a release position and a blocked position and being biased toward the blocked position by engagement of a resilient member of the clip with a wall of the housing such that movement of the clip toward the release position deforms the resilient member and generates a force urging the clip back toward the blocked position;
applying a force to the clip;
moving the clip from the blocked position to the release position against the bias toward the blocked position as a result of the applied force;
inserting the at least a portion of the connecting element into the housing;
releasing the applied force on the clip; and
moving the clip from the release position to the blocked position under the bias toward the blocked position to capture the at least a portion of the connector element in the housing and thereby secure the orthodontic appliance to the patient.

15. The method of claim 14, wherein moving the clip from the blocked position to the release position comprises moving the clip along the first linear translation axis in a direction toward the housing, and moving the clip from the release position to the blocked position comprises moving the clip along the first linear translation axis in a direction away from the housing.

16. The method of claim 14, wherein the connector element is inserted into the housing in an insertion direction and wherein moving the clip from the blocked position to the release position comprises moving the clip along the first linear translation axis in a direction that is generally perpendicular to the insertion direction.

17. The method of claim 14, further comprising maintaining a threshold level of bias away from the release position when the clip is in the blocked position.

18. The method of claim 14, wherein the clip has a central aperture with a first aperture portion and a second aperture portion, the first aperture portion intersecting the second aperture portion and being larger than the second aperture, wherein the housing includes an aperture configured to receive the connector element therethrough, and wherein moving the clip from the blocked position to the release position further comprises aligning the first aperture portion with the aperture in the housing.

* * * * *